United States Patent
Brissonneau (10) Patent No.: US 12,241,858 B2
(45) Date of Patent: Mar. 4, 2025

(54) OXYGEN POTENTIOMETRIC PROBE, FOR THE MEASUREMENT OF THE OXYGEN CONCENTRATION OF A LIQUID METAL, APPLICATION TO THE MEASUREMENT OF OXYGEN IN LIQUID SODIUM OF A NUCLEAR REACTOR OF TYPE RNR-NA

(71) Applicant: COMMISSARIAT A L'ENERGIE ATOMIQUE ET AUX ENERGIES ALTERNATIVES, Paris (FR)

(72) Inventor: Laurent Brissonneau, Venelles (FR)

(73) Assignee: COMMISSARIAT A L'ENERGIE ATOMIQUE ET AUX ENERGIES ALTERNATIVES, Paris (FR)

(*) Notice: Subject to any disclaimer, the term of this patent is extended or adjusted under 35 U.S.C. 154(b) by 26 days.

(21) Appl. No.: 17/304,276

(22) Filed: Jun. 17, 2021

(65) Prior Publication Data
US 2021/0396707 A1  Dec. 23, 2021

(30) Foreign Application Priority Data
Jun. 17, 2020 (FR) ...................................... 20 06323

(51) Int. Cl.
*G01N 27/411* (2006.01)
*G01N 33/2025* (2019.01)
(Continued)

(52) U.S. Cl.
CPC ..... *G01N 27/4112* (2013.01); *G01N 27/4118* (2013.01); *G01N 33/2025* (2019.01); *G01N 33/205* (2019.01); *G21C 17/025* (2013.01)

(58) Field of Classification Search
CPC ........... G01N 27/4112; G01N 27/4118; G01N 33/2025; G01N 33/205; G01N 27/409;
(Continued)

(56) References Cited

U.S. PATENT DOCUMENTS 5,043,053 A * 8/1991 Indig .................... G01N 27/301
204/435
6,181,760 B1 * 1/2001 JinKim .................. G21C 17/00
324/71.2
(Continued)

FOREIGN PATENT DOCUMENTS

CN 106248760 A * 12/2016 ......... G01N 27/4076
CN 109590635 A * 4/2019
(Continued)

OTHER PUBLICATIONS

Jung et al., English translation of DE2350485A1, 1975 (Year: 1975).*

(Continued)

*Primary Examiner* — Luan V Van
*Assistant Examiner* — Shizhi Qian
(74) *Attorney, Agent, or Firm* — Oblon, McClelland, Maier & Neustadt, L.L.P.

(57) ABSTRACT

A potentiometric oxygen sensor for measuring an oxygen concentration of a liquid metal, which includes a metal tube forming at least one sensor body part, an electrochemical subassembly, and an insert made of a transition metal from group 4 of the Periodic Table or its alloy. The electrochemical subassembly contains an electrolyte, intended to be in contact with the liquid metal, and a reference electrode contained in the electrolyte, the electrolyte being made of yttrium-doped or calcium-doped hafnia ($HfO_2$), or of thoria ($ThO_2$), which is optionally yttrium-doped or calcium-doped, or of yttrium-doped or calcium-doped zirconia (Continued)

($ZrO_2$). The reference electrode contains at least one metal and its oxide form at the operating temperature of the potentiometric oxygen sensor. The insert is arranged between the sensor body part and the electrolyte, and is attached to the sensor body part and brazed onto the electrolyte by a brazing joint.

16 Claims, 3 Drawing Sheets

(51) Int. Cl.
*G01N 33/205* (2019.01)
*G21C 17/025* (2006.01)
(58) Field of Classification Search
CPC ....... G21C 17/025; Y02E 30/10; Y02E 30/30; G21B 1/25
See application file for complete search history.

(56) References Cited

U.S. PATENT DOCUMENTS

| | | | |
|---|---|---|---|
| 2002/0015463 A1* | 2/2002 | Kim | G21C 17/00 376/305 |
| 2017/0307560 A1* | 10/2017 | Oba | G01N 27/4062 |
| 2019/0031571 A1* | 1/2019 | Sandin | B23K 1/00 |

FOREIGN PATENT DOCUMENTS

| | | | |
|---|---|---|---|
| DE | 2 304 485 A1 | | 8/1974 |
| DE | 2350485 A1 | * | 4/1975 |
| FR | 2 325 928 A1 | | 4/1977 |
| FR | 2 659 739 B1 | | 5/1992 |
| JP | S5652257 U | * | 5/1981 |
| JP | H11118754 A | * | 4/1999 |
| JP | 2000335981 A | * | 12/2000 |
| JP | 2004294131 A | * | 10/2004 |
| JP | 2018-025421 A | | 2/2018 |
| WO | WO 2015/092317 A1 | | 6/2015 |

OTHER PUBLICATIONS

Takahashi et al., English translation of JP2004294131A, 2004. (Year: 2004).*
Tsunoda et al., English translation of JPH11118754A, 1999 (Year: 1999).*
Takahashi et al., Corrosion Behavior of Various Ceramics in Sulfuric Acid, Journal of the Ceramic Society of Japan, 1995, 103 (1203), 1205-1207. (Year: 1995).*
Liu et al., Adjustable thermal expansion properties in Zr2MoP2O12/ ZrO2 composites, Frontiers in Chemistry, 2018, 6, 347 (Year: 2018).*
Komura, English translation of JPS5652257U, 1981 (Year: 1981).*
Aerts et al., Oxygen-iron interaction in liquid lead-bismuth elutectic alloy, PCCP, 2016, 18, 19526 (Year: 2016).*
Nollet, Development of electrochemical oxygen sensors for liquid sodium, IAEA 2013, https:/inis.iaea.org/collection/NCLCollectionStore/_Public/45/089/45089513.pdf (Year: 2013).*
Bassini, Coolant chemistry control in heavy liquid metal cooled nuclear systems, PhD thesis, University of Bologna, 2017 (Year: 2017).*
Shin et al., Development of electrochemical oxygen sensor for high temperature sodium environment application, Transactions of the Korean Nuclear Society Spring Meeting, Jeju, Korea, May 17-18, 2012 (Year: 2012).*
Konys et al., Electrochemical oxygen sensors for corrosion control in lead-cooled nuclear reactors, NACE Corrosion 2009, paper # 09421 (Year: 2009).*
Zirconium, Technical data for Zirconium, https://periodictable.com/ Elements/040/data.html, evidence for claim 1, 2024 (Year: 2024).*
An et al., CN109590635A, English translation, 2019 (Year: 2019).*
Hori et al. , JP2000335981A, English translation, 2000 (Year: 2000).*
Brissonneau, "New considerations on the kinetics of mass transfer in sodium fast reactors: An attempt to consider irradiation effects and low temperature corrosion", Journal of Nuclear Materials, Elsevier, 2012, vol. 423, 26 total pages.
Mason et al., "The monitoring of oxygen, hydrogen and carbon in the sodium circuits of the PFR", Liquid Metal Engineering and Technology, BNES, 1984, pp. 53-59.
Osterhout, "Operating Experience with On-Line Meters at Experimental Breeder Reactor-II (EBR-II)", LIMET Liquid Metal Technology, 1980, pp. 15-19-15-15 (7 total pages).
Fouletier et al., "Potentiometric Sensors for High Temperature Liquids", Materials Issues for Generation IV Systems, 2008, pp. 445-459.
Jayaraman et al., "Review—Evolution of the Development of In-Sodium Oxygen Sensor and Its Present Status", Journal of the Electrochemical Society, 2016, vol. 163, No. 7, pp. B395-B402.
Roy et al., "Electrochemical Oxygen Sensor for Measurement of Oxygen in Liquid Sodium", Nuclear Technology, vol. 39, 1978, pp. 216-218.
French Preliminary Search Report issued May 18, 2021 in French Application 20 06323 filed on Jun. 17, 2020, 3 pages (with English Translation of Categories of Cited Documents).
Courouau et al., "$HfO_2$-based electrolyte potentiometric oxygen sensors for liquid sodium", Electrochimica Acta, 331, 135269, 2020, 14 pages.

* cited by examiner

OXYGEN POTENTIOMETRIC PROBE, FOR THE MEASUREMENT OF THE OXYGEN CONCENTRATION OF A LIQUID METAL, APPLICATION TO THE MEASUREMENT OF OXYGEN IN LIQUID SODIUM OF A NUCLEAR REACTOR OF TYPE RNR-NA

CROSS-REFERENCE TO RELATED APPLICATIONS

The present claims the benefit of the filing date of French Appl. No. 20 06323, filed on Jun. 17, 2020, the content of each of which is incorporated by reference.

TECHNICAL FIELD

The present invention relates to a potentiometric oxygen sensor for measuring the oxygen concentration (content) of a liquid metal.

The main application targeted for the sensor according to the invention is the measurement of the oxygen concentration of the liquid sodium in a primary loop of a fast neutron reactor cooled with liquid metal, such as liquid sodium, known as SFR (Sodium Fast Reactor) and which forms part of the family of fourth-generation reactors.

Although described with reference to the main application, the potentiometric sensor according to the invention may be used in any application which requires measurement in a medium which is at high temperature and/or which is highly reductive and/or subject to high pressures, and notably sodium in a secondary loop of an SFR reactor, as a redundant means for detecting a risk of sodium-water reaction (SWR), or a liquid metal other than sodium, such as lead and alloys thereof in which the corrosion of steels is a pronounced phenomenon. Another application that may be envisaged for a potentiometric oxygen sensor according to the invention concerns concentrating solar power stations, for which the measurement of oxygen is not predominant to date due to their operating temperatures which remain limited, typically at about 550° C., but which might be predominant if said temperatures were higher, this being currently under study for yield enhancement purposes.

PRIOR ART

In a sodium-cooled nuclear reactor, it is imperative to be able to perform reliable measurement of the oxygen content. Specifically, the French specifications concerning the reactor stipulate that this content be less than 3 ppm in the primary loop, when the reactor is in operation. The aim of this requirement is to limit the corrosion kinetics of the cladding, which are more or less proportional to the oxygen content, and thus the release of activated corrosion products into the liquid sodium circuit. These phenomena are described, for example, in greater detail in publication [1].

Essentially two techniques are known for measuring the oxygen content of the sodium in SFR reactors.

The first is an indirect technique which consists of a purity measurement by means of a clogging indicator which determines the "clogging" temperature, below which the precipitation of sodium oxide and hydride crystals commences. Such a clogging indicator is described, for example, in patent FR 2 659 739 B1.

This indirect technique has the major drawback of not measuring only the oxygen content, but all of the impurities present in the sodium. It is therefore representative of the oxygen content only if the sodium is free of other impurities. Furthermore, it requires a treatment time of several hours.

The second technique consists in using a potentiometric oxygen sensor either directly in the main tank of an SFR reactor [2], or in a dedicated loop [3], or on the purification loop.

Typically, the operating temperature of the sensor is thus between 350° C. and 450° C. The expected service life for a sensor must be at least of the order of 18 months.

This time corresponds to the periods between two long stoppages for the refueling of a unit of a nuclear reactor. Thus, it is envisaged to change the sensors during a long stoppage, which makes it possible to conserve the degree of availability of the unit concerned.

A potentiometric sensor has the major advantage of measuring only the oxygen content. It is thus specific, and affords redundancy and independence relative to the measurement of the clogging indicator of the indirect technique. Furthermore, it is much more rapid, or even theoretically virtually in real time.

The structure of such a sensor and its functioning are described, for example, in publication [4]. Patent application JP2018025421 describes a sensor for measuring the concentration of a gas, in particular of oxygen, in a molten metal, in particular liquid copper.

Thus a potentiometric oxygen sensor in sodium functions on the principle of measuring an electrical potential difference due to a difference in oxygen activity in two media separated by an electrolyte.

The potential difference between the medium studied (sodium) and the reference medium (with a fixed oxygen activity) is linked to the oxygen activity in the two media via the Nernst law as follows:

$$\Delta E = 4 \frac{\mathcal{F}}{\mathcal{R}T} \ln \frac{a_O^{Na}}{a_O^{ref}}$$

in which $\mathcal{F}$ is the Faraday constant, $\mathcal{R}$ the ideal gas constant, T the temperature in degrees Kelvin and $a_O^{Na}$ the oxygen activity in sodium which is proportional to the oxygen concentration and $a_O^{ref}$ the oxygen activity in the reference medium.

The electrolyte used in a potentiometric sensor must be a purely ionic conductor of oxygen ions and resistant to corrosion both by sodium and the reference medium. From a practical viewpoint, there are very few ion-conducting oxides that are resistant to corrosion by sodium: these are doped thorium or hafnium oxides. As highlighted in publication [5], yttrium-doped thoria is the electrolyte that has been the most commonly used, yttrium being used to dope thoria by increasing the ion conduction by means of creating oxygen holes.

One of the difficulties encountered for making a potentiometric sensor consists in achieving leaktightness with respect to sodium, between the ceramic electrolyte part of the sensor and the pipework of the sodium circuit. Specifically, it is impossible to use conventional systems on the ceramic electrolyte brought to a temperature above 200° C.

One simple method consists in making a solidified sodium joint by creating a temperature gradient along the sensor. The sealing between the reference and the exterior is then achieved using conventional joints at temperatures below 100° C. It has the drawback of subjecting to a high thermal gradient a long ceramic tube, said material generally being subject to fragility under this constraint and for the low thickness required for its function as an electrolyte.

An alternative method consists in brazing a small electrolyte onto a metallic sensor body. Sealing may then be achieved by means of metal flanges that are resistant to high temperatures. The use of the sensor on the pipes becomes much more flexible and this configuration limits the risks of breakage, in particular during thermal shocks. The difficulty is, however, transferred onto the brazed area, which must be robust and resistant to corrosion by sodium.

Patent FR 2 325 928 B1 describes a potentiometric oxygen sensor, the thoria ($ThO_2$) electrolyte of which doped with yttrium oxide is brazed on its periphery inside a metal tube made of stainless steel or nickel. In publication [6] in the name of the inventors of the abovementioned patent FR 2 325 928 B1, it was proposed to solve the problem of the differences in coefficient of expansion between yttrium-doped thoria and stainless steel by using an intermediate brazing made of Fe—Co—Ni alloy with a controlled coefficient of thermal expansion. In this publication [6] and in the abovementioned patent FR 2 325 928 B1, the brazing chosen is based on Fe—Co—Ni alloy in order to be able to perform molybdenum Mo metallization so as, according to the inventors, to achieve the brazing per se. Patent application WO 2015/092317 A1 discloses a reactive brazing assembly process using Fe—Ni alloys with additions of Ti or Zr. However, the tests that were performed on a sensor obtained by means of this process on an yttrium-doped hafnia electrolyte (simulating thoria) or based on yttrium-doped thoria showed possibilities of fissuring of the ceramic.

In general, as listed in the table on page 3 of publication [5], a large number of defects was observed for the existing sensors with an electrolyte based on thoria, in particular at the electrolyte/metal alloy bond interface.

These defects do not make it possible to envisage the perennial use of potentiometric oxygen sensors under extreme conditions of use.

Patent application DE 230485 A1 describes a potentiometric oxygen sensor notably for measuring the oxygen content in a molten metal (cf. paragraph 5), the ceramic electrolyte of which is brazed to a metal tube by an insert with a brazing joint, which, like publication [6] and the abovementioned patent FR 2 325 928 B1, is chosen as an Fe—Co—Ni alloy. In the preferred example, the brazing joint chosen is made of Ni—Cu alloy for its ductility, i.e. the ease with which it makes the brazing penetrate between the components to be assembled. The insert material chosen does not enable it to achieve eutectic melting. Consequently, the solution according to DE 230485 A1 has the major drawbacks firstly of having melting of the brazing at very high temperatures and secondly of having an insert material which has a coefficient of expansion that follows the ceramic electrolyte only in a low temperature range which remains limited, typically to a maximum of 600° C. However, in the context of the problem, it may occur that the brazing is performed at a temperature at 1100° C. A sensor according to said document thus has the same shortcomings with the same associated risks of failure as the existing sensors mentioned above.

There is thus a general need to improve the existing potentiometric oxygen sensors, notably so that they can take reliable measurements over a considerable period, under temperature and pressure conditions of liquid sodium in an SFR nuclear reactor configuration.

The aim of the invention is to at least partly meet this need.

DESCRIPTION OF THE INVENTION

To do this, the invention concerns, in one of its aspects, a potentiometric oxygen sensor for measuring the oxygen concentration of a liquid metal, notably a molten metal in a nuclear reactor, comprising:
  a metal tube forming at least one sensor body part;
  an electrochemical subassembly comprising an electrolyte, intended to be in contact with the liquid metal, and a reference electrode contained in the electrolyte, the electrolyte being made of yttrium-doped or calcium-doped hafnia, or of thoria, which is optionally yttrium-doped or calcium-doped, or of yttrium-doped or calcium-doped zirconia, the reference electrode comprising at least one metal and its oxide form at the operating temperature of the sensor;
  an insert made of a transition metal from group 4 of the Periodic Table or an alloy thereof, arranged between the sensor body part and the electrolyte, the insert being attached to the sensor body part and brazed onto the electrolyte by a brazing joint, the coefficient of thermal expansion of the insert being close to the coefficient of thermal expansion of the electrolyte and below the coefficient of thermal expansion of the sensor body part, the stiffness of the insert being higher than the stiffness of the sensor body part.

Thus, the invention consists essentially in arranging an insert which acts as an intermediate part between the sensor body and the electrolyte, the insert material being astutely chosen in relation with the metallic material both of the sensor body and the ceramic material of the electrolyte to make it possible to reverse the nature of the brazing filler metal in comparison with that which is performed in the potentiometric oxygen sensors according to the prior art. Consequently, the invention enables leaktight assembly between sensor body and electrolyte with good mechanical properties due to the insert which notably absorbs the mechanical stresses, and especially reduces them due to the low difference in coefficient of expansion over a wide temperature range, and with an insert/electrolyte interface that is free of cracks. In other words, the invention makes it possible to solve a large number of crack defects which have been observed for the ceramic/metal bonds of the sensors according to the prior art.

By means of this guaranteed absence of defects, it is possible to envisage reliable and long-lasting oxygen content measurements even under extreme temperature and pressure conditions encountered in a nuclear reactor cooled with liquid sodium.

The inventor went against a widespread prejudice. Specifically, to date, a person skilled in the art invariably considered that, in order to perform a difficult assembly which is intended to be used in a highly hazardous environment, such as in a bath of molten metal, it was imperative to use alloys of the Fe—Co—Ni type, as in patent application DE 230485 A1 cited in the preamble. This is explained by the fact that these alloys can be metallized and brazed, often with a fragile material, like glass, mentioned as an example in patent application DE 230485 A1.

In other words, a person skilled in the art had not even envisaged performing tests with other Fe—Co—Ni alloys in the context of a potentiometric oxygen sensor.

The term "yttrium-doped hafnia" means a material composed of at least 50% by mass of $HO_2$—$Y_2O_3$, and preferably at least 90% by mass of $HfO_2$—$Y_2O_3$, and even more preferentially at least 95% of $HfO_2$—$Y_2O_3$.

The term "calcium-doped hafnia" means a material composed of at least 50% by mass of $HfO_2$—CaO, and preferably at least 90% by mass of $HO_2$—CaO, and even more preferentially at least 95% of $HfO_2$—CaO containing not more than 33% by mass of CaO relative to the $HfO_2$.

The term "yttrium-doped thoria" means a material composed of at least 50% by mass of $ThO_2$—$Y_2O_3$, and preferably at least 90% by mass of $ThO_2$—$Y_2O_3$, and even more preferentially at least 95% of $ThO_2$—$Y_2O_3$ containing not more than 33% by mass of $Y_2O_3$ relative to the $HfO_2$.

The term "calcium-doped thoria" means a material composed of at least 50% by mass of $ThO_2$—CaO, and preferably at least 90% by mass of $ThO_2$—CaO, and even more preferentially at least 95% of $ThO_2$—CaO containing not more than 33% by mass of CaO relative to the $ThO_2$.

The term "yttrium-doped zirconia" means a material composed of at least 50% by mass of $ZrO_2$—$Y_2O_3$ and preferably at least 90% by mass of $ZrO_2$—$Y_2O_3$, and even more preferentially at least 95% of $ZrO_2$—$Y_2O_3$.

In each of these materials, the percentages remaining relative to the mass percentages indicated above may correspond to one or more other oxides included in the composition of the electrolyte. These elements make it possible to modify the properties of the electrolyte (ion conductivity, mechanical strength, etc.). The electrolyte may also be reinforced with particles of other materials, for example $Al_2O_3$ fibers.

Preferably, the yttrium-doped hafnia comprises from 0.5% to 30% by mass of yttrium oxide.

Preferably, the yttrium-doped zirconia comprises from 0.5% to 20% by mass of yttrium oxide.

Preferably, the yttrium-doped thoria comprises from 0.5% to 30% by mass of yttrium oxide.

Preferably, the calcium-doped thoria comprises from 0.5% to 20% by mass of calcium oxide.

Preferably, the calcium-doped zirconia comprises from 0.5% to 20% by mass of calcium oxide.

Preferably, the calcium-doped hafnia comprises from 0.5% to 20% by mass of calcium oxide.

For illustrative purposes, the table below indicates coefficients of thermal expansion, between 20° C. and 900° C., for various materials.

TABLE 1

| | |
|---|---|
| Alumina | $8.1 \times 10^{-6}$ per ° C. |
| Zirconia | $8.9 \times 10^{-6}$ per ° C. |
| Yttria-stabilized zirconia | $11 \times 10^{-6}$ per ° C. |
| Hafnia | $7.5 \times 10^{-6}$ per ° C. |
| Thoria | $8.7 \times 10^{-6}$ per ° C. |
| Ferritic stainless steel | $12.7 \times 10^{-6}$ per ° C. |
| Austenitic stainless steel | $19.6 \times 10^{-6}$ per ° C. |
| Inconel 718 alloy | $17.2 \times 10^{-6}$ per ° C. |
| Titanium | $10.2 \times 10^{-6}$ per ° C. |
| Zirconium | $7.4 \times 10^{-6}$ per ° C. |

The coefficients of thermal expansion of the ceramics are markedly lower than those of the stainless steels (in particular austenitic steels) or the nickel bases. The coefficients of expansion of the transition metals, and in particular of zirconium, are closer to the coefficients of the ceramics.

According to an advantageous embodiment, the sensor also comprises a retaining ring, arranged both around the insert and the sensor body part, the ring being adapted to hold said objects during the production of the brazing joint.

The first function of this ring is to hold the insert and the lower sensor body during brazing.

Preferably, the retaining ring is made of a material whose coefficient of thermal expansion is close to that of thoria or of hafnia, preferably an iron-nickel (Fe—Ni) alloy.

According to an advantageous embodiment variant, the sensor body comprises two tubular parts, the lower part being the one attached to the electrolyte and the upper part being intended to project outside the liquid metal, the two tubular parts being assembled together by means of a metallic joint connector, the male part of which is integrally fastened to the end of the lower or upper part of the sensor body and, respectively, the female part of which is integrally fastened to the end of the upper or lower part of the sensor body.

According to another advantageous embodiment, the sensor also comprises an openwork metal sheath arranged around the electrolyte, the openwork sheath being adapted to allow the liquid metal to pass through. The presence of this openwork sheath enables protection of the electrolyte during the handling of the sensor and prevents the dispersion of shards in the liquid metal in the event of breakage.

Advantageously, the openwork sheath is attached to the ring, preferably by screwing.

The insert may advantageously be protected from corrosion by being coated with a metal coating, for example made of nickel.

Advantageously, the insert and the electrolyte have coefficients of thermal expansion which vary by not more than 30%, preferably not more than 20%.

The metal sensor body advantageously has corrosion resistance properties in the medium under consideration. The sensor body is advantageously adapted to be used in a molten metal and/or in a reductive medium, notably in liquid sodium.

Advantageously, the sensor body and, where appropriate, the openwork sheath and the sensor fixing flange are made of stainless steel, preferably ferritic or austenitic steel, or of a nickel-based alloy. The term "nickel-based" means that nickel is the predominant element, which may range, for example, from 50% to 80% by mass. These materials are highly resistant to corrosion by the medium under consideration, even under stress. Nickel-based alloys and austenitic stainless steels are highly resistant to corrosion in liquid sodium Na at the temperatures under consideration. Typically, the sensor body and, where appropriate, the openwork sheath and the sensor fixing flange are made of 304L or 316L type stainless steel. Advantageously, the transition metal of the insert is zirconium (Zr), hafnium (Hf) or titanium (Ti).

The brazing joint may be made of nickel (Ni) or of copper (Cu) as a nickel-copper alloy containing at least 50% by mass of nickel or containing at least 50% by mass of copper. When the joint is made of nickel, the brazing is advantageously performed at a temperature ranging from 980° C. to 1060° C. and preferably from 1000° C. to 1040° C. When the brazing joint is made of copper, the brazing is advantageously performed at a temperature ranging from 930° C. to 990° C. and preferably from 950° C. to 970° C.

Advantageously, the material of the reference electrode, which should preferentially be in liquid form at the operating temperature of the sensor, is made of indium (In) in equilibrium with its oxide form ($In_2O_3$), or of bismuth (Bi) in equilibrium with its oxide form ($Bi_2O_3$), or of gallium (Ga) in equilibrium with its oxide form ($Ga_2O_3$) or of sodium in equilibrium with its oxide form ($Na_2O$).

According to an advantageous variant, the sensor body houses a measuring head suitable for measuring the electrical potential difference in the reference electrode and also for measuring the temperature. Advantageously, the measuring head may incorporate at least one thermocouple.

Preferably, the measuring head suitable for electrical measurement of the potential difference in the reference electrode is made of molybdenum (Mo) or consists of electrical wires, preferably electrically insulated from the sensor body by means of a sheath made of electrically insulating material, preferably alumina ($Al_2O_3$).

A subject of the invention is also a potentiometric oxygen sensor as described previously, the sensor body being made of stainless steel, the insert being made of zirconium, the electrolyte being made of yttrium-doped or calcium-doped hafnia ($HfO_2$) or of yttrium-doped or calcium-doped thoria ($ThO_2$), for measurement of the concentration of oxygen in liquid sodium or in lead-lithium (Pb—Li) eutectic alloy, preferably at operating temperatures of between 250° C. and 450° C.

A subject of the invention is also a potentiometric oxygen sensor as described previously, the sensor body being made of stainless steel, the insert being made of titanium, the electrolyte being made of zirconia, for measuring the concentration of oxygen in liquid lead and its alloys with heavy metals (Pb—Bi, etc.).

A subject of the invention is a nuclear fission reactor cooled with liquid metal (sodium, lead, or alloys thereof such as lead-bismuth), lead-lithium, comprising at least one potentiometric oxygen sensor as described previously.

Finally, a subject of the invention is a nuclear fusion reactor comprising at least one potentiometric oxygen sensor as described previously.

It may be a nuclear fusion reactor in which the extraction of heat and the production of tritium are produced by tritium-generating coverings cooled with Pb—Li.

Other advantages and features of the invention will emerge more clearly on reading the detailed description of examples of implementation of the invention which are given as nonlimiting illustrations in reference to the following figures.

DETAILED DESCRIPTION

It is pointed out here that throughout the present patent application, the terms "lower", "upper". "over", "under", "inner", "outer", "internal" and "external" should be understood with reference to a potentiometric sensor according to the invention in the vertically fixed operating configuration, in longitudinal cross section view along its longitudinal axis of symmetry X.

Figure 1:
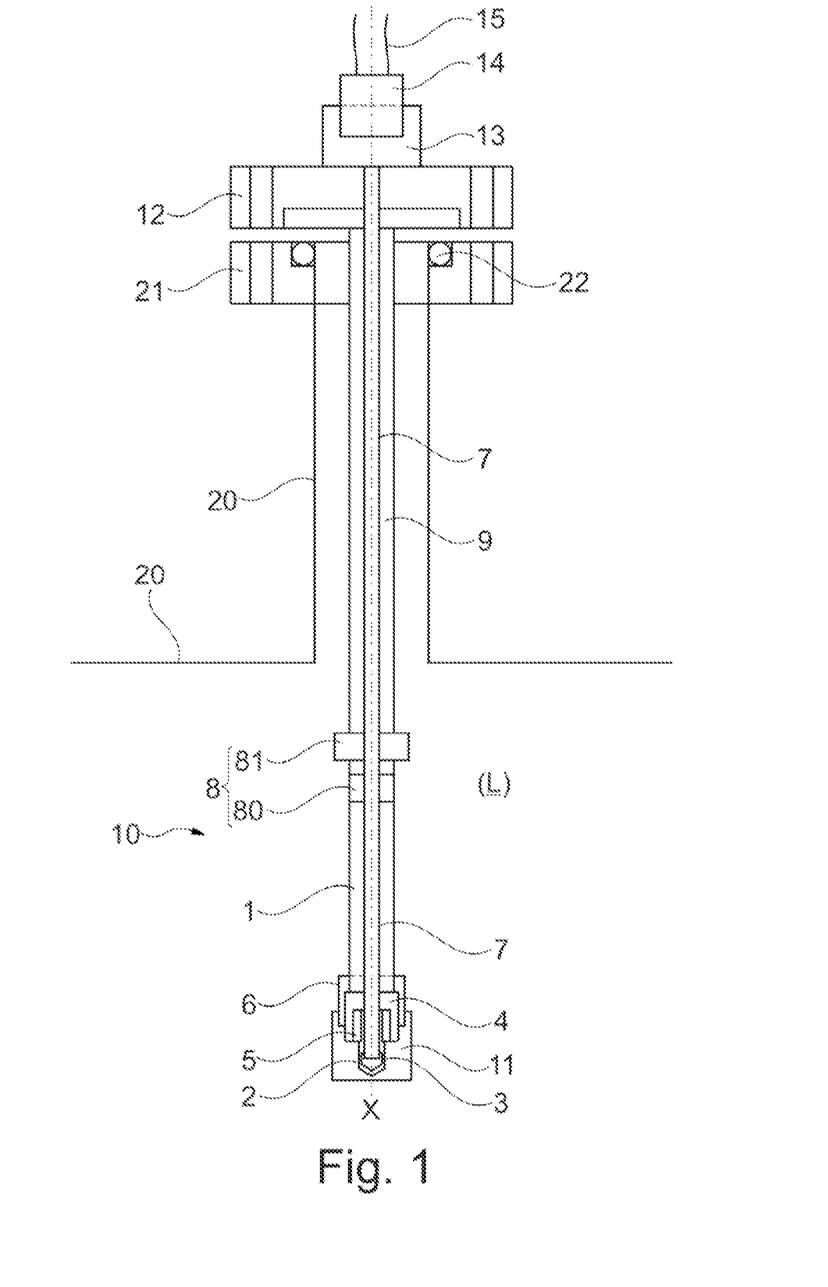
FIG. 1 is a schematic view in longitudinal cross section of a potentiometric oxygen sensor, the figure showing the sensor positioned on and attached to a pipe containing the liquid metal for which the sensor is intended to measure the oxygen concentration.

FIG. 1 shows a potentiometric oxygen sensor 10 according to the invention, of axisymmetric form about a central axis X.

As illustrated, this sensor 10 is attached to a wall 20 of a pipe containing a liquid metal (L), typically liquid sodium, under the temperature and pressure conditions encountered in a primary loop of an SFR reactor, the oxygen content of which it is desired to measure.

This sensor 10 first comprises a tubular sensor body, the lower tube 1 of which is intended during functioning to be immersed in the liquid metal, and the upper tube 9 of which is intended to project outside the liquid metal (L). The tubes 1, 9 of the sensor body are made, for example, of 304L or 316L type stainless steel.

The lower end of the sensor 1 comprises a container 2 constituting an electrolyte made of yttrium-doped or calcium-doped hafnia ($HfO_2$), or of thoria ($ThO_2$), which is optionally yttrium-doped or calcium-doped, or of yttrium-doped or calcium-doped zirconia ($ZrO_2$). As illustrated, the electrolyte 2 is preferably configured in the form of a pocket.

The electrolyte contains a material 3 forming a reference electrode. This material 3, which should preferentially be liquid at the operating temperature of the sensor, is made of indium (In) and in its oxide form ($In_2O_3$), or of bismuth (Bi) and in its oxide form ($Bi_2O_3$), or of gallium (Ga) and in its oxide form ($Ga_2O_3$) or of sodium and in its oxide form ($Na_2O$).

According to the invention, the sensor 10 comprises an insert 4 made of zirconium (Zr), hafnium (Hf) or titanium (Ti), arranged between the lower tube 1 of the sensor body and the electrolyte 2. This insert 4 is, on the one hand, attached to the tube 1 and, on the other hand, brazed onto the electrolyte 2 by a brazing joint 5.

As stated hereinbelow, the brazing joint 5 is produced by a brazing filler made of nickel, copper or an alloy thereof (Ni—Cu) in the form of a strip or at least of a wire or of a deposit applied beforehand of the brazing onto the inside diameter of the insert 4.

To ensure the attachment of the insert 4 to the lower tube 1 of the sensor body, a retaining ring 6 arranged around these two parts 1, 4 is provided. This ring 6 also makes it possible to hold these parts during the production of the brazing joint 5. Preferentially, this ring 6 is made of Fe—Ni or FeNi—Co alloy with coefficients of expansion close to that of the insert 4 and of the electrolyte 2.

The measuring head 7 of the sensor is housed inside the sensor body 1, 9 and comes into contact with the material 3 forming the reference electrode. This measuring head 7 thus makes it possible to measure the electrical potential difference in the reference electrode 3. Advantageously, it may be envisaged for it also to measure the temperature. The sensitive element(s) of the measuring head are made of molybdenum or electrical wires. Preferably, this (these) sensitive element(s) are housed in a ceramic sheath, such as an alumina sheath, so as to ensure the electrical insulation with the metal tubes 1, 9 of the sensor body.

The two tubes 1, 9 of the sensor body are assembled together by means of a metallic joint connector 8. As illustrated, this metallic joint connector 8 is envisaged to be arranged in the liquid metal (L). This connector, preferably made of stainless steel, with a metallic joint 8, preferably made of copper or nickel, advantageously makes it possible to perform a brazing leaktightness test. This test is performed, for example, by connecting a helium leakage detector onto the connector. A vacuum is produced in the sensor body by means of the detector pump, and helium is then injected outside the sensor. In the event of leakage, helium penetrates into the sensor body and is sucked toward the detector counter. Care is obviously taken to have very good leaktightness at the connection onto the sensor body, so as not to generate an artificial leak.

In the example illustrated, the male part 80 of the connector 8 is welded to the upper end of the lower tube 1 and the female part 81 is welded to the lower end of the upper tube 9 of the sensor body. The reverse arrangement may, of course, be envisaged.

An openwork metal sheath 11, in the form of an end cap which allows the liquid metal to pass through, is screwed onto the retaining ring 6, being arranged around the electrolyte 2. This openwork sheath 11 enables, on the one hand, protection of the electrolyte 2 during the handling of the sensor and, on the other hand, prevents the dispersion of shards in the liquid metal in the possible event of breakage. The openwork sheath 11 is made, for example, of 304L or 316L type stainless steel.

To ensure leaktight attachment of the sensor during functioning to the pipe 20, a fixing flange 12 welded to the upper end of the tube 9 of the sensor body is attached by screwing to a fixing flange 22 of the pipe 20. In order to ensure leaktightness, a metallic O-ring 22 is arranged in the fixing flange 22 of the pipe. The fixing flanges 12, 22 are made, for example, of 304L or 316L type stainless steel.

A metal connector 13 is screwed onto the top of the fixing flange 12 so as also to hold by screwing a connector 14 of the measuring head 7 from which the electrical measuring wires lead toward an electrical connection of a high-impedance voltmeter.

The various successive steps of the process for manufacturing a potentiometric sensor 10 according to the invention which has just been described are now described.

Step a/: the brazing filler 5 is placed in contact inside the insert 4. The brazing filler 5 is made in the form of a strip and/or at least of a wire made of nickel, copper or an alloy thereof (Ni—Cu) if it is not already present as a deposit on the insert 4.

Step b/: fitting of the container forming the electrolyte 2 into the insert 4 is performed.

Step c/: the insert 4 and the lower tube 9 of the sensor body are attached together, by means of the retaining ring 6.

Step d/: brazing is then performed between the electrolyte 2 and the insert 4 according to the following process.

A heat treatment above the melting point of the lowest-melting eutectic of the system consisting of the insert 4 material and the brazing filler 5 is first performed, so as to melt the latter, which, after cooling, forms the brazing joint 5.

The brazing thermal cycle successively includes: a temperature rise, a steady stage at the brazing temperature ("high" stage) and a cooling ramp down to a temperature below the melting point of the brazing. Preferably, the cooling is performed down to room temperature. The term "room temperature" means a temperature of the order of 20 to 25° C.

The steady stage at the brazing temperature is, for example, of the order of about 10 minutes (for example from 10 minutes to 30 minutes).

The brazing temperature is below the melting points of the materials to be assembled. More particularly, it is above the theoretical temperature of the lowest-melting eutectic (transition metal of the insert 4—brazing filler). This makes it possible to enrich the liquid present at the interface with transition metal.

Advantageously, brazing is performed at a moderate temperature to limit the thermomechanical stresses due to the cooling after the assembly cycle. The assembly produced may be used up to temperatures of the order of 900° C.

Preferably, advantageously, the steady-stage temperature is at least 40° C. above the eutectic formation temperature. For example, for a brazing filler made of pure nickel, a steady stage at about 1000° C. will be chosen, and for a brazing filler made of copper, a steady-stage temperature of about 930° C. will be chosen.

The brazing is preferably performed in an oxygen-free environment, for example by brazing under secondary vacuum (for example at a total pressure of $10^{-5}$ mbar) or under an oxygen-purified neutral gas.

Hafnia and thoria are particularly stable ceramics that are very difficult to reduce in comparison with other ceramics such as $Al_2O_3$ or $ZrO_2$. It was notably observed, unexpectedly, that zirconium reduces these ceramics and that the oxygen obtained from this reduction dissolves in the brazing 5, and also possibly a little in the insert 4.

Zirconium is not only an active element that is capable of partially reducing a ceramic at elevated temperature, but also makes it possible to obtain a brazing composition that is capable of forming, for example, with nickel, copper and iron eutectics below 1000° C.

The absence of a layer of oxide of the group 4 transition metal at the interface with the electrolyte 2 is ensured by sufficient dilution of this metal in the brazing element 5 and the insufficient time during the brazing cycle to form this layer. Thus, relative to the conventional reactive brazing processes, this layer is not formed due to the fact that the brazing filler is not in direct contact with the electrolyte 2 and that the oxygen is dissolved in a large amount of the joint filler due to the presence of the insert.

To illustrate the brazing according to this step d/, an electrolyte 2 made of yttrium-doped hafnia is produced and is brazed with an insert made of zirconium 4.

The electrolyte made of yttrium-doped hafnia 2 is a pocket with a tubular part having an outside diameter of 10 mm.

The zirconium insert 4 has a tubular part with an outside diameter of 12.5 mm.

The brazing filler is introduced in the form of a wire 0.45 mm in diameter and 7 mm long. It is an Ni201 wire.

The brazing filler is placed at the two ends of the brazing zone (a turn of wire at each end, introduced into a groove).

Figure 2:
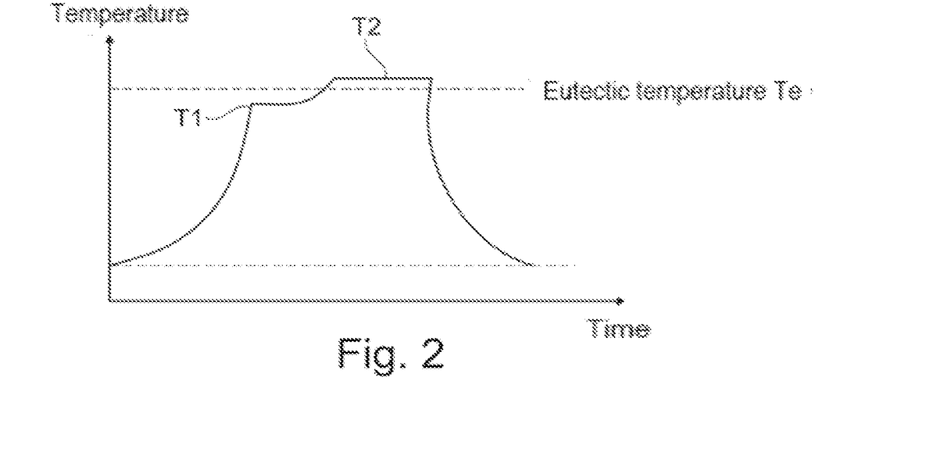
FIG. 2 is a graph representing the curve of temperature as a function of time during a brazing step to produce a sensor according to the invention.

The thermal cycle performed for the brazing is shown in the graph illustrated in FIG. 2. In this cycle, the temperature increase is stopped at a steady stage, just below the eutectic temperature (Te), to homogenize the temperature, for example for 30 minutes at 900° C. Typically, the homogenization temperature T1 may be below Te−20° C. The steady stage may be from 10 to 30 minutes at a brazing temperature, T2, equal to Te+40° C.

Figure 3:
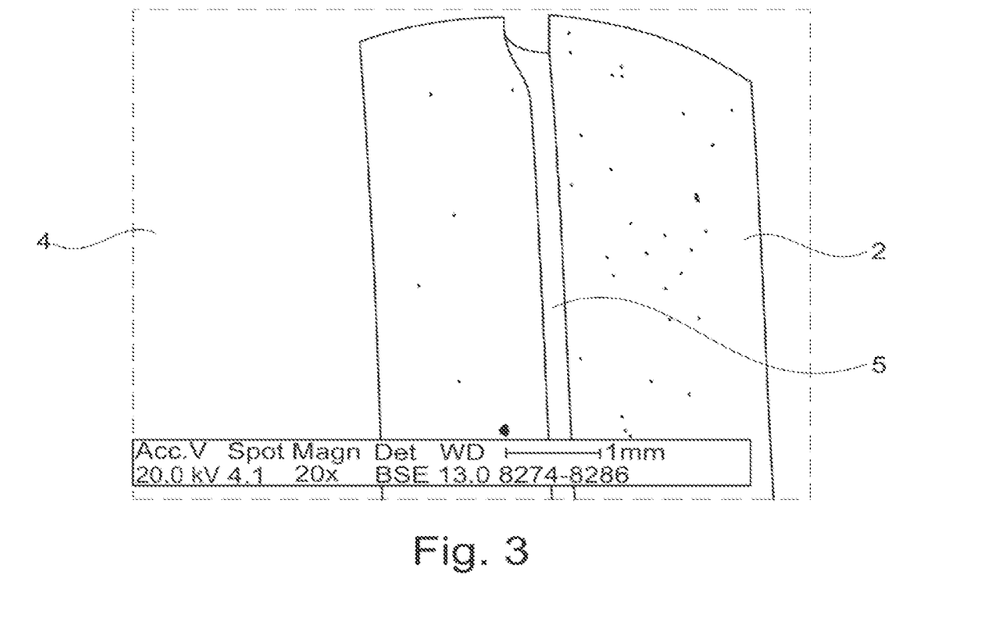
FIG. 3 is an image obtained by scanning electron microscopy, at the interface of a brazing joint made of a nickel alloy and of an electrolyte made of yttrium-doped hafnia of a sensor according to the invention.
Figure 4:
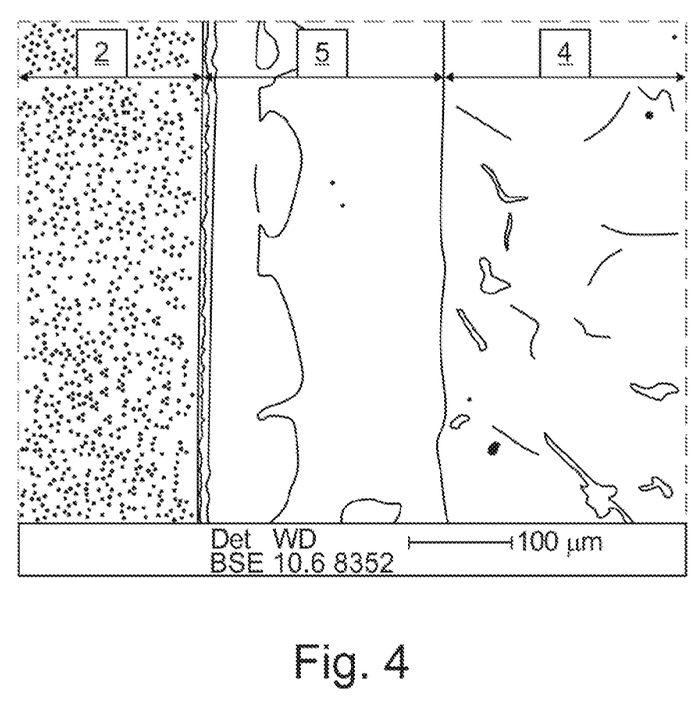
FIG. 4 is also an image obtained by scanning electron microscopy, with magnification relative to the preceding figure, at the interface of a brazing joint made of a nickel alloy and of an electrolyte made of yttrium-doped hafnia of a sensor according to the invention.

FIGS. 3 and 4 show the interface obtained between the resulting brazing joint 5 and the electrolyte 2.

Observation of the structure of this bonding zone shows the absence of interface cracks. The inner tube electrolyte 2 made of yttrium-doped hafnia, the brazing joint 5 and the outer insert 4 made of zirconium are seen, from right to left in FIG. 3 and from left to right in FIG. 4. A strong reserve of pure zirconium is observed close to the interface. Sufficient dilution of the zirconium tube in the brazing which forms during the steady stage at high temperature, and also the greater attraction for oxygen of zirconium than of nickel, result in this configuration, which proved to be favorable for an absence of cracks at the brazing/electrolyte interface.

Step e/: once the brazing is finished, the electrolyte 2 undergoes reoxidation by circulating a slightly oxidizing gas, for example <1% of $O_2$ in argon, at a temperature of between 500 and 800° C.

Step f/: the openwork sheath 11 is attached by screwing onto the retaining ring 6.

Step g/: in order to check the leaktightness of the sensor assembly, a helium leakage test is performed.

Step h/: once the leakage test has been passed, the material 3, i.e. the metal and its oxide form, forming the reference electrode is introduced into the bottom of the pocket 2 by passing it inside the lower tube 1 of the sensor body.

Step i/: the fixing flange 12 is then welded onto the upper tube 9 of the sensor body.

Step j/: the upper tube 9 is assembled with the lower tube 1 of the sensor body by means of the connector, the leaktightness being achieved by means of the metallic joint of the connector 8.

Step k/: finally, the measuring head 7 is introduced into the sensor body 1, 9, the leaktightness being achieved by means of the screwed connector 13 at the end of the upper tube 9 of the sensor body.

The installation and functioning of a potentiometric sensor 10 according to the invention that has just been described are performed as follows.

Step 1/: the sensor 10 is introduced into an empty pipe 20, i.e. a pipe containing no liquid metal, the leaktightness being achieved at the flange of the pipe 12, 21 by means of the joint 22.

Step 2/: the temperature of the pipe 20 is raised beyond the melting point of the liquid metal.

Step 3/: once this melting point has been exceeded, the pipe 20 is filled with liquid metal (L).

Step 4/: the liquid metal is then raised to the desired temperature.

Step 5/: a potential measurement is taken with a high-impedance potentiometer between the measuring head 7 and the emerging part of the upper tube 9 of the sensor body, and a temperature measurement is taken on the thermocouple of the measuring head 7.

Step 6/: the oxygen activity in the liquid metal (L) can then be deduced from the Nernst law, recalled in the preamble.

Other variants and improvements may be applied without, however, departing from the scope of the invention.

The potentiometric oxygen sensor according to the invention may be used for measuring the oxygen content of a liquid metal, which may be sodium (Na) or a sodium-potassium (Na—K) alloy, or lead (Pb), or a lead-bismuth (Pb—Bi) alloy or a lead-lithium (Pb—Li) alloy.

The invention is not limited to the examples that have just been described; features of the illustrated examples may notably be combined together within variants not illustrated.

LIST OF CITED DOCUMENTS

[1] L. Brissonneau, "*New considerations on the kinetics of mass transfer in sodium fast reactors: An attempt to consider irradiation effects and low temperature corrosion*", Journal of Nuclear Materials, 423 (2012), pp 67-78.

[2] Mason, L., N. S. Morrison, and C. M. Robertson. "*The monitoring of oxygen, hydrogen and carbon in the sodium circuits of the PFR. in Liquid Metal Engineering and Technology*". 1984. Oxford.

[3] Osterhout, M. M. "*Operating experience with on-line meters at experimental breeder reactor II (EBR II). in LIMET Liquid Metal Technology*". 1980. Richland, USA, J. M. Dahlke.

[4] Fouletier, J. and V. Ghetta, "*Potentiometric sensors for high temperature liquids, in Materials Issues for Generation IV Systems*", V. Ghetta, Editor. 2008, Springer Science. pages 445-459.

[5] Jayaraman, V., Gnanasekaran, T., 2016. "*Review—Evolution of the Development of In-Sodium Oxygen Sensor and Its Present Status*". J. Electrochem. Soc. 163, B395-B402.

[6] Roy, J. C. and B. E. Bugbee, "*Electrochemical oxygen sensor for measurement of oxygen in liquid sodium*". Nuclear Technology 1978. 39: pages 216-218.

The invention claimed is:

1. A potentiometric oxygen sensor configured for measuring an oxygen concentration of a liquid metal, the sensor comprising:
   a metal tube forming at least one sensor body part;
   an electrochemical subassembly comprising an electrolyte, configured to be in contact with the liquid metal, and a reference electrode contained in the electrolyte, the electrolyte being made of yttrium-doped hafnia, calcium-doped hafnia, thoria optionally doped with yttrium or calcium, yttrium-doped zirconia, or calcium-doped zirconia, the reference electrode comprising a reference electrode metal and an oxide form of the reference electrode metal at an operating temperature of the potentiometric oxygen sensor; and
   an insert made of hafnium or hafnium alloy, arranged between the at least one sensor body part and the electrolyte, the insert being attached to the at least one sensor body part and brazed onto the electrolyte by a brazing joint,
   wherein the insert has a first coefficient of thermal expansion,
   wherein the at least one sensor body part has a second coefficient of thermal expansion, and
   wherein the first coefficient of thermal expansion is below the second coefficient of thermal expansion.

2. The sensor of claim 1, further comprising:
   a retaining ring, arranged both around the insert and the at least one sensor body part,
   wherein the retaining ring is adapted to hold the insert and the at least one sensor body part during a production of the brazing joint.

3. The sensor of claim 2, wherein the retaining ring is made of an iron-nickel alloy.

4. The sensor of claim 1, wherein the at least one sensor body part comprising a first tubular part and a second tubular part,
   wherein a lower part of the first and second tubular parts being attached to the electrolyte and an upper part of the first and second tubular parts being configured to project outside the liquid metal,
   wherein the first and second tubular parts are assembled together by a metallic joint connector,
   wherein a male part of the metallic joint connector is integrally fastened to an end of the lower or upper part of the at least one sensor body part, and
   wherein, respectively, a female part of the metallic joint connector is integrally fastened to an end of the upper or lower part of the at least one sensor body part.

5. The sensor of claim 1, further comprising:
an openwork metal sheath arranged around the electrolyte,
wherein the openwork metal sheath is adapted to allow the liquid metal to pass through.

6. The sensor of claim 5, further comprising:
a retaining ring, arranged both around the insert and the at least one sensor body part,
wherein the retaining ring is adapted to hold the insert and the at least one sensor body part during a production of the brazing joint, and
wherein the openwork metal sheath is attached to the retaining ring.

7. The sensor of claim 6, wherein the openwork metal sheath is attached to the retaining ring by screwing.

8. The sensor of claim 1, wherein the brazing joint is made of nickel.

9. The sensor of claim 1, wherein the at least one sensor body part houses a measuring head suitable for measuring an electrical potential difference in the reference electrode and also for measuring a temperature.

10. A measurement method, comprising:
measuring a concentration of oxygen in liquid sodium or in lead-lithium eutectic alloy with the potentiometric oxygen sensor of claim 1,
wherein the at least one sensor body part is made of stainless steel, and
wherein the electrolyte is made of yttrium-doped hafnia, calcium-doped hafnia, yttrium-doped thoria, or calcium-doped thoria.

11. The method of claim 10, wherein the measuring is operated at a temperature in a range of from 250° C. to 450° C.

12. A measurement method, comprising:
measuring a concentration of oxygen in liquid lead, or a lead alloy comprising a heavy metal, with the potentiometric oxygen sensor of claim 1,
wherein the at least one sensor body part is made of stainless steel, and
wherein the electrolyte is made of zirconia.

13. A nuclear fission reactor, comprising:
the potentiometric oxygen sensor of claim 1,
wherein the nuclear fission reactor is cooled with liquid metal.

14. A nuclear fusion reactor, comprising:
the potentiometric oxygen sensor of claim 1.

15. The sensor of claim 1, wherein the insert is made of hafnium.

16. The sensor of claim 1, wherein the brazing joint is made of copper.

* * * * *